United States Patent [19]

Kalvinsh et al.

[11] Patent Number: 4,568,689

[45] Date of Patent: Feb. 4, 1986

[54] PHARMACEUTICAL PREPARATION FOR THE TREATMENT OF HYPERTENSIVE DISEASE AND MYOCARDIAL INFARCTION

[76] Inventors: Ivars Y. Kalvinsh, ulitsa Miera, 17, kv. 8, Salaspils; Marina L Erenshtein, ulitsa Lielvardes, 127, kv. 7, Riga; Gunar A. Bremanis, ulitsa 1905 goda, 18, Jurmala; Valdis D. Mikazhan, ulitsa Talavas Gatve, 5, kv. 40, Riga; Maris M. Veveris, ulitsa Veyavas, 10/2, kv. 20, Riga; Edmund Y. Lukevits, ulitsa Ierikju, 43, kv. 10, Riga; Edit A. Pule, ulitsa Bauskas, 11, kv. 8, Riga; Anatoly S. Birman, ulitsa Kirova, 24, kv. 8, Riga, all of U.S.S.R.

[21] Appl. No.: 610,634

[22] Filed: May 16, 1984

[30] Foreign Application Priority Data

May 18, 1983 [SU] U.S.S.R. ................. 3593392

[51] Int. Cl.$^4$ ..................................... A61K 31/415
[52] U.S. Cl. ..................................... 514/404; 514/929
[58] Field of Search ................. 424/273 P; 514/929, 514/404

[56] References Cited

U.S. PATENT DOCUMENTS 3,974,176 8/1976 Rainer ........................ 424/273 P
4,018,890 4/1977 Möller et al. ................ 424/273 P

FOREIGN PATENT DOCUMENTS 2605243  9/1976  Fed. Rep. of Germany ... 424/273 P
47-20160 9/1972  Japan ............................. 424/273 P
2073740A 10/1981 United Kingdom .
0747855  7/1980  U.S.S.R. ........................ 424/273 P

OTHER PUBLICATIONS

Chem. Abstracts 94:65536q, (1981).
Chem. Abstracts 82:57691y, (1975).
Dalton et al., "The Reactions of Some 1,1-Dialkylhydrazines with Unsaturated and Bromo Aliphatic Acids", Aust. J. Chem. 1980, 33, 1365-1372.

*Primary Examiner*—Allen J. Robinson
*Attorney, Agent, or Firm*—Burgess, Ryan & Wayne

[57] ABSTRACT

A novel pharmaceutical preparation for the treatment of hypertensive disease and myocardial infarction, which comprises as an active ingredient, (1,1-dimethyl-3-oxopyrazolidin-1-io-4-yl)acetate of the following formula:

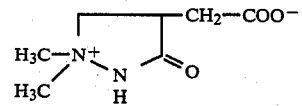

and a pharmaceutically acceptable vehicle.

8 Claims, No Drawings

PHARMACEUTICAL PREPARATION FOR THE TREATMENT OF HYPERTENSIVE DISEASE AND MYOCARDIAL INFARCTION

FIELD OF THE INVENTION

The present invention relates to the medicine and, more particularly, to a novel pharmaceutical preparation for the treatment of hypertensive disease and myocardial infarction.

BACKGROUND OF THE INVENTION

For prophylaxis and treatment of myocardial infarction a wide range of well-known preparations is used, namely: organic nitrates and nitrites, $\beta$-adreno-blockers, analgetic agents, anticoagulating and fibrinolytic agents, antiarrhythmic and cardiotonic preparations and, quite recently, calcium antagonists.

To reduce the arterial pressure and lower the heart load, preparations with different mechanisms of action are used. Neurotropic hypotensive preparations affect various units of the nervous regulation: cholinolytic preparations lower the muscular tension of the organs having cholinergic innervation, antiadrenergic preparations lower the tension of a number of organs and systems having adrenergic innervation. However, it is rather difficult to administer such preparations in the case of an acute cardiac insufficiency, as well as in the post-infarction state.

Preparations of a central sedative effect (sedatives, tranquilizers, soporific agents) restrict the flow of efferent nervous pulses, thus resulting in a reduced arterial pressure and a lowered oxygen demand of the heart. However, their protracted administration is accompanied by the development of adaptation and narcomania. Ganglioblockers, while inhibiting propagation of excitation in sympathetic and parasympathetic ganglia, exert a hypotensive effect, but their administration is contraindicated in the case of an accute heart insufficiency and post-infarction state.

Known are various $\beta$-adrenoblockers such as inderal, benzodixin, oxyprenolol; they, however, feature a number of side phenomena. These preparations are toxic ($LD_{50}$ for inderal is 30 to 50 mg/kg for white mice). They also have a negative inotropic effect; contraindicated for a number of cardiac diseases such as sinus bradycardia, bronchial asthma and the like; they can also cause allergic responses.

Among calcium antagonists an evergrowing use enjoys the preparation nifedipine. However, its effect likewise that of other preparations of this group, is not sufficiently long (no longer than 8 hours) which necessitates a three-times daily administration thereof. Furthermore, discontinuation of the administration of the preparation results in a recurrence of hypertension and a higher consumption of oxygen.

Also known in the art is a naturally-occurring alkaloid stachydrine (1,1-dimethylpyrrolidin-1-io-2-yl)formate (cf. Rodina L. G., Determination of the Pharmacological Effect of Some Components of Leonorus Guingulobatus, Pharmacia, 1968, 17 (2), 55–58).

This alkaloid is recovered from Leonorus extract and has a hypotensive effect. This compound, however, considerably lowers the number of cardiac contractions (by 19% on the average), thus substantially limiting the possibilities of its application. Furthermore, stachydrine sharply changes the blood coagulability.

Known in the art is a compound-(1,1-diemthyl-3-oxopyrazolidin-1-io-4-yl)acetate (cf. L. K. Dalton, S. Demeral, B. S. Elmes. The reactions of some 1,1-dialkylhydrazines with unsaturated and bromoaliphatic acids, Aust. J. Chem., 1980, 17(2), 55–58).

Biological activity of this compound has not been hitherto described in the literature.

SUMMARY OF THE INVENTION

It is an object of the present invention to provide a novel pharmaceutical preparation for the treatment of hypertensive disease and myocardial infarction which would have a high activity, long duration of its effect, a low toxicity and absence of side phenomena.

The pharmaceutical preparation for the treatment of hypertensive disease and myocardial infarction is novel and hitherto unknown from the literature.

This object is accomplished according to the present invention by administering the instant pharmaceutical preparation for the treatment of hypertensive disease and myocardial infarction comprising an active principle and a pharmaceutically acceptable vehicle contains, according to the invention, as the active principle, (1,1-dimethyl-3-oxopyrazolin-1-io-4-yl)acetate of the following formula:

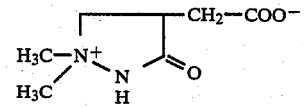

The pharmaceutical preparation according to the present invention for the injectional administration preferably contains the active principle in an amount of from 1 to 2.5% by weight. As the pharmaceutically acceptable vehicle it preferably contains distilled water or an isotonic solution. For the peroral or sublingual administration the preparation according to the present invention preferably contains the active principle in an amount of 0.4–0.45 g per tablet or capsule. For the peroral and sublingual administration it is preferred that as the pharmaceutically acceptable vehicle starch, Aerosil (registered trademark of DeGussa, Inc., Frankfurt, Germany for a pyrogenic silica) and magnesium stearate be used.

DETAILED DESCRIPTION OF THE INVENTION

The hypotensive effect of the preparation according to the present invention, as well as its acute toxicity and effect on survival of test animals were studied on an neoepinephrine model of infarction.

The study of the hypotensive effect was carried out in experiments on spontaneously hypertensive male rats of the Akamoto-Aoki line aged 20–25 weeks. The prior art preparation-nifedipine was used for the purpose of comparison. The measurement of the arterial pressure was effected on the tail vein of the rats by the indirect method. The animals were divided into groups (10 in each) and trained for two weeks with the view to ensure their adaptation to the unit for the measurement of the arterial pressure. The level of the arterial pressure prior to administration of the test preparations was measured three times: two days, one day and directly prior to administration of the test preparations. The preparation was administered in the form of a 2.5% aqueous solution, nifedipine—in the form of a 2.5% suspension in Twin-80 intraperitoneally. The arterial pressure was measured 30 minutes, 1,2,4 and 24 hours after the administration. The test results are shown in Table 1 hereinbelow.

Thus, even 30 minutes after the intraperitoneal administration of the studied preparation in the dose of 50 mg/kg the systolic and diastolic pressure values are reduced by 17.6 and 23.5% respectively, whereas

TABLE 1

Effect of the preparation of this invention and nifedipine on arterial pressure of rats with spontaneous hypertension

| Nos | Preparation | Dose, mg/kg intraperitoneally | Variation of arterial pressure, % of the initial upon expiration of | | | | | | | | |
|---|---|---|---|---|---|---|---|---|---|---|---|
| | | | 30 minutes | | 1 hour | | 2 hours | | 4 hours | | 24 hours | |
| | | | S* | D** | S | D | S | D | S | D | S | D |
| 1 | 2 | 3 | 4 | 5 | 6 | 7 | 8 | 9 | 10 | 11 | 12 | 13 |
| 1 | Nifedipine | 1 | −4 | −8 | −11 | −14 | −8 | −21 | −11 | −31 | 0 | 0 |
| 2 | Preparation of this invention | 50 | −17 | −23 | −12 | −28 | −18 | −26 | −21 | −41 | −17 | −19 |
| | | 25 | −3 | −1 | −5 | −7 | −3 | −19 | −7 | −18 | — | — |

*Systolic pressure
**Diastolic pressure

Acute toxicity measurements were carried out in experiments on white mongrel mice upon intraperitoneal administration. The $LD_{50}$ of the preparation according to the present invention is 2,239 (1,279–3,917) mg/kg.

Also studied was the efficiency of the oral form of the preparation according to the present invention. Hypertensive rats were per os administered with an aqueous suspension of the preparation according to the present invention at such a rate that the concentration of the active principle be not more than 2.5%. The efficiency was studied within the range of doses from 50 to 100 mg/kg. Measurements of the arterial pressure were effected on expiration of 0.5, 1, 2, 4 and 24 hours after administration of the preparation. The results of these investigations are shown in Table 2 hereinbelow.

nifedipine (1 mg/kg) intraperitoneally) by this time lowers the systolic pressure by 4.3%, and the diastolic pressure—by 7.6%. The maximum efficiency regarding the reduction of pressure in the case of nifedipine is observed on the fourth hour after administration of the preparation, whereafter the effect of the pressure reduction is considerably lowered and upon expiration of 8 hours the effect of nifedipine is substantially discontinued. At the same time, the preparation according to the present invention on expiration of 24 hours after a single-time administration still ensures an effective reduction of the arterial pressure (systolic—by 18.8% and diastolic—by 28.5%). Therefore, to maintain a steady therapeutic effect it is necessary to administer nifedipine not rarely than 3 times a day, whereas the frequency of administration of the preparation according to the pres-

TABLE 2

Effect of the oral form of the preparation of this invention on arterial pressure of spontaneously hypertensive rats upon a single-time administration

| Nos | Preparation | Dose, mg/kg | Variation of arterial pressure, % of the initial upon expiration of | | | | Variation of arterial pressure, % of the initial upon expiration of | | | | | |
|---|---|---|---|---|---|---|---|---|---|---|---|---|
| | | | 30 minutes | | 1 hour | | 2 hours | | 4 hours | | 24 hours | |
| | | | S* | D** | S | D | S | D | S | D | S | D |
| 1 | 2 | 3 | 4 | 5 | 6 | 7 | | | | | | |
| 1 | Preparation this invention | 50 | −3 | −10 | ±0 | +2 | −5 | −8 | −3 | −3 | −7 | −2 |
| 2 | Preparation this invention | 75 | −16 | −12 | −10 | −17 | −18 | −18 | −8 | −11 | −20 | −22 |
| 3 | Preparation this invention | 100 | −13 | −11 | −7 | −8 | −8 | −7 | −13 | −13 | −12 | −3 |
| 4 | Nifedipine | 10 | −10 | −14 | −14 | −18 | −10 | −16 | −18 | −20 | 0 | 0 |

*Systolic pressure
**Diastolic pressure

The hypotensive preparation according to the present invention has a low toxicity ($LD_{50}$ is 2,239 mg/kg intraperitoneally to white mice); it is not only highly efficient in doses equal to 1/50 and below of the $LD_{50}$ which ensures safety of its administration, but it also increases the difference between systolic and diastolic pressures (see Table 1).

The preparation according to the present invention has the following advantages over nifedipine: a lower toxicity (the $LD_{50}$ of nifedipine upon its administration intraperitoneally to white mice is 185 mg/kg), a rapid action and a more prolonged hypotensive effect.

ent invention is only once a day which provides considerable advantages in the case of a long-time ambulatory administration of the preparation.

In the per os method of administration the most effective is the dose of 75 mg/kg causing a stable reduction of the arterial pressure by about 20% even 24 hours after administration of the preparation, i.e. as regards the duration of its action, the latter preparation is by at least 3 times superior over the prior art preparation—nifedipine.

The study of the effect produced by the preparation according to the present invention on survival of animals with a neoepinephrine model of infarction was effected in comparison with the prior art preparations—obzidan and finoptin.

The formation of a neoepinephrine model of infarction (focal necrosis) of myocardium in rats was effected by way of an every-day subcutaneous administration of a 0.1% solution of neoepinephrine in the dose of 3 mg/kg for 7 days to rats of the Wistar line with a mass of 160–200 g. The test preparations were subcutaneously administered to the rats in the form of a 1.25% aqueous solution in the dose of 25 mg/kg 0.5 hour after injection of neoepinephrine also for 7 days. The animals were observed for 19 days and the account of survival was recorded in groups initially counting 12 animals each. The test results are shown in Table 3 hereinbelow.

TABLE 3

Study of the effect of the preparations on survival of rats with the neoepinephrine model of infarction

| Preparation | Dose, mg/kg | Number of survived animals after 19 days | Percentage of survival |
|---|---|---|---|
| Control | | | |
| (Distilled water) | — | 4 | 33 |
| Obzidan | 25 | 6 | 50 |
| Finoptin | 25 | 6 | 50 |
| Preparation of this invention | 25 | 11 | 92 |

The effect of the pharmaceutical preparation according to the present invention on the arterial pressure and vegetative responses was studied in acute experiments on cats with a mass of 2.8–4.0 kg narcotized with α-glucochloralose (90 mg/kg) and urethane (100 mg/kg, intraperitoneally). The breathing, arterial pressure in the common carotid artery and electrocardiogram of the second standard lead were recorded.

The influence of the preparation according to the present invention on hemodynamic effects of acetylcholine (0.1 μg/kg) neoepinephrine (0.2 μg/kg), noradrenaline (1 μg/kg), histamine (1.5 μg/kg) and angiotensin (0.1 μg/kg) was also studied. The preparation of this invention was intravenously administered in the form of a 2.5% solution in doses of 0.5 to 10 mg/kg. The peripheral part of the vagus nerve was irritated by supromaximum pulses with the frequency of 30 Hz and duration of 0.1 ms.

It has been found that the preparation according to the present invention when administered intravenously within the studied range of doses does not substantially affect the breathing and electrocardiogram of the animals. The effect of the preparation on responses to the administration of biogenic amines is shown in Table 4 hereinbelow.

It follows from the above Table 4 that the preparation according to the present invention in higher doses (10 mg/kg) substantially blocks both α- and β-receptors, as well as the cholinergic system, while at the same time it does not provide any direct influence on effects of angiotensin and histamine. The administration of the preparation according to the present invention results in reduction of peripheral resistance which is one of the factors defining the hypotensive effect of the preparation.

A comparative study of the effects produced by the preparation according to the present invention and finoptin on an experimental necrosis of myocardium caused by introduction of adrenaline.

The experiments were carried out on rats of the Wistar line of gregarious keeping, both sexes, with a mass of 170 to 225 g. Each preparation was studied on a separate group of animals: (group of adrenaline-control, group of finoptin, group of the preparation according to the present invention). 72 rats were used in the experiments altogether. Injuries of myocardium were caused by way of a single-time subcutaneous administration of a 0.1% solution of adrenaline hydrochloride in the dose of 3 mg per kg of the rat's bodyweight. The preparation according to the invention and finoptin were administered daily for 5 days in the dose of 25 mg/kg in the form of a 1.25% solution. The preparation of this invention was administered subcutaneously, finoptin-per os. On the first day of the experiment the preparations were administered 30 minutes after injection of adrenaline hydrochloride. The experiment lasted for 19 days. Slaughters were effected on the 4th, 8th, 12th and 19th day of the experiment. The animals were decapitated. The heart was fixed in a 10% solution of neutral formalin and sealed in paraffin. Serial sections with the thickness of 5–6μ were coloured by Ehrlich hematoxylin-eosin. The state of vessels of myocardium, cardiomyocytes and interstitial tissue were evaluated by histological analysis.

In the control group animals a characteristic pattern of an adrenaline injury of myocardium was observed on the 4th day of the experiments. In some animals in coronary vessel walls focal necroses were observed more or less intensively pronounced, as well as infiltration of the adventitia of coronary vessels with lymphoid cells. A non-uniform distribution of endothelium cells is observed in walls of arteries of individual vessels. Nuclei of cardiomyocytes adjacent to the altered coronary vessels are in the stage of pyknosis, cells—in the state of granular-lumpy decomposition. In the injured regions of cardiomyocytes combination of acid dyes is enhanced (eosinophilia). In the majority of the animals necrosis covers 3–5 cells in the wall of the left ventricle. In the wall of the left ventricle the granular-lumpy

TABLE 4

Effect of the preparation of this invention on the arterial pressure and vegetative responses in narcotized animals

| Nos 1 | Dose of the preparation of this invention, mg/kg 2 | Variation of arterial pressure, % 3 | Variation of acetylcholine effect 4 | Hemodynamic effect, in % | | | |
|---|---|---|---|---|---|---|---|
| | | | | Noradrenaline 5 | Neoepinephrine 6 | Angiotensine 7 | Histamine 8 |
| 1 | 0.5–3.0 | ±0 | ±0 | −10 | 0 ÷ −10 | ±0 | ±0 |
| 2 | 5 | −16 | ±0 | −10 ÷ −15 | 0 ÷ −10 | ±0 | ±0 |
| 3 | 10 | −5 ÷ −10 | −15 ÷ −20 | −20 ÷ −25 | −35 | ±0 | ±0 | decomposition is revealed diffusively in substantially all cells and alterations of the contracture type are observed.

The interstitial tissue is edematous and round-cell infiltrates are formed around necrotized muscular fibres. In the subendocardial layer of the left ventricle wall a plurality of granulomae are observed.

In myocardium of the rats administered with the preparation according to the present invention the left ventricle capillaries are plethoric. In two cases insignificant infiltrations of the adventitia with lymphoid cells are observed. The granular-lumpy decomposition, necrosis of 3-5 cells is observed in a half of the investigated animals. The formation of granulomae on the side of the interstitial tissue is observed in all of the animals.

The morphological pattern of myocardium in the rats administered with finoptin is the following: injuries of the vascular system are less clearly pronounced as compared to adrenaline; non-uniform distribution of endothelium and infiltration of adventita of arteries with lymphoid cells are insignificant; granular-lumpy decomposition and pyknosis of nucleiis less pronounced than in the control group animals. This phenomenon is observed in a half of the animals. Necrosis and eosinophilia, as well as contracture alterations of muscular cells are observed in a half of the studied animals. On the part of the interstitial tissue: edema is decreased, in a half of the animals a diffusive round-cell infiltration is observed, the formation of granulomae is similar to that of the animals of the control group.

It should be noted that only in the control group (adrenaline) pathology of muscular cells around the coronary arteries was observed. On the 8th day of the experiment as compared to the 4th day of the experiment the necrobiotic areas in the walls of coronary vessels of the control group animals decreased, but the number of lymphoid cells in the adventitia was slightly increased. Certain changes could be found in endothelial cells in the form of swelling of the cells and their projection into the inner space of the vessels. Changes on the side of cardiomyocytes: granular-lumpy decomposition is more limited as compared to the 4th day (more localized). Cells with signs of necrosis (coagulation—later stage of necrosis) as compared to the 4th day constitute 3-5 cells. Eosinophilia and contracture type pathologies are more clearly pronounced than on the 4th day.

Changes on the part of the interstitial tissue: diffusive round-cell infiltration in the stroma is decreased. A scarring tissue with elastic fibres appears.

In the group of animals administered with the preparation according to the present invention on the 8th day the coronary vessels are without changes; in some cases insignificantly plethoric vessels and changes in cells in the form of swelling are observed. Changes on the part of cardiomyocytes: the granular-lumpy decomposition is considerably lowered as compared to the 8th day of the control group animals (adrenaline) and decreased as compared to the 4th day of the experiment. Eosinophilia and contracture type changes in cardiomyocytes were slightly increased as compared to the 4th day of the experiment. These morphological changes are the result of a more pronounced coagulation necrosis which is developed in the dynamics of transformation of necrotic cells. As compared to the 8th day of the control group (adrenaline) these changes are much less pronounced.

Changes on the part of the interstitial tissue: the formation of the scarring tissue is to a lesser extent than in the control group.

In the group of animals administered with finoptin an insignificant infiltration of adventitia of vessels with lymphoid cells (half of the test animals) is observed on the 8th day of the experiment; on the part of endothelial cells—more pronounced swelling as compared to the group of animals administered with the preparation according to the present invention.

Changes on the part of cardiomyocytes:

granular-lumpy decomposition, eosinophilia and contructure type pathology are more pronounced than in the group of animals administered with the preparation according to the present invention, but less pronounced as compared to the control group (adrenaline). As compared to the 4th day of the experiment these alterations are enhanced which is associated with a natural transformation of necrotized cardiomyocytes in the development of the myocardial infarction.

Changes on the part of the interstitial tissue:

a more intensive growth of the scarring tissue is observed as compared to the group of animals administered with the preparation according to the present invention and an insignificant decrease as compared to the control group (adrenaline).

On the 12th day of the experiment in the control group (adrenaline) a more clear stabilization of the process in the injured areas is observed as compared to the 8th day of the experiment and the process of injury in the myocardium is not deepened. It should be noted that in the interstitial tissue the scarring tissue becomes more coarse (which further results in cardiosclerosis) The growth of the connective tissue (young) occurs which is the most intensive by the 19th day.

On the part of myocardial vessels and cardiomyocytes no essential changes were found on the 12th day of the experiment in comparison with the 19th day.

In the group of animals administered with the preparation according to the present invention an insignificant plethora of the vessels is observed on the 12th day of the experiment. By the 19th day this phenomena becomes more clearly pronounced.

Changes on the part of cardiomyocytes:

no essential difference is observed on the 12th day of the experiment as compared to the 19th day. In comparison with the 8th day of the experiment eosinophilia and contructure type changes are decreased.

Changes on the part of the interstitial tissue:

the scarring tissue formation is more distinctly pronounced. These changes are substantially less revealed than the changes in the control group (adrenaline).

In the group of animals administered with finoptin on the 12th day of the experiment certain changes are observed on the part of endothelial cells (swelling). Changes on the part of cardiomyocytes: stabilization of the process is observed. Eosinophilia is retained and the contructure type changes are more clearly pronounced than in the group administered with the preparation according to the present invention. By the 19th day these changes are getting less noticeable.

Changes on the part of the interstitial tissue:

an intensive formation of the scarring tissue occurs more noticeably than in the group of animals administered with the preparation according to the present invention.

On the 19th day of the experiment in the group of animals administered with adrenaline (control) a less-pronounced infiltration with lymphoid cells is retained in the animals; in a number of cases changes on the part on endothelium of vessels are observed, the granular-lumpy decomposition retains, necroses covering 3-5 cells are less pronounced than on the 4th day of the experiment, eosinophilia and contructure type changes are also retained, on the part of the interstitial tissue the propagation of a coarse connective tissue is observed in all of the animals.

In the group administered with the preparation according to the present invention on the 19th day of the experiment no changes were noticed on the part of the coronary vessels. The plethora of capillaries in the left ventricle wall is noticed. In half of the animals the granular-lumpy decomposition is less pronounced. Necrosis of individual cells and eosinophilia, as well as contructure type changes are also observed. On the part of the connective tissue a less pronounced formation of the scarring tissue is to be noted as compared to the control group.

In the group of animals administered with finoptin no changes are detected on the part of the coronary vessels on the 19th day of the experiment. In half of the animals a moderately pronounced granular-lumpy decomposition is retained along with eosinophilia, cell necroses and contructure type changes.

The results of the investigations are shown in Table 5.

Comparing the data obtained on the 4th, 8th, 12th and 19th day of the experiment, it should be noted that the preparation according to the present invention possesses a clearly manifested therapeutic effect allowing no significant changes in the myocardium, prevents the growth of the scarring tissue, contributes to the restoration of morphological structures of the myocardium.

The preparation according to the present invention can be administered in various pharmaceutical forms: injection solutions, tablets, capsules. The pharmaceutical forms are prepared by conventional methods. The active principle of the preparation according to the present invention is obtained following a known procedure. As the solvent for the injection solutions it is preferred to use distilled water or an isotonic solution. For the purpose of injections it is preferable to use a 1-2.5% solution of the active principle.

As the filler for tablets and capsules it is preferable to use starch, Aerosil, magnesium stearate. Methyl- or ethyl-cellulose can be also used. Any pharmaceutically acceptable fillers can be used. The content of the active principle in tablets and capsules is preferably 0.4-0.45 g.

The preparation according to the present invention is administered once a day in the dose of 0.4-0.45 g. The treatment course is 10 days.

No side effects or contraindications for administration of the preparation according to the present invention have been revealed.

TABLE 5

| Nos | 1 | 2 | 3 | 4 |
|---|---|---|---|---|
| 1 | Day of the experiment | 4th day | 4th day | 4th day |
| 2 | Number of animals | 6 | 6 | 6 |
| 3 | Groups | adrenaline (control) | adrenaline + the preparation of this invention | adrenaline + finoptin |
| | Changes in the myocardium vessels | | | |
| 4 | (1) plethora of the vessels | 0/4    ++/2 | 0/2 ++/2 +++/2 | 0/2 ++/2 +++/2 |
| | (2) wall necrosis | 0/6 | 0/6 | 0/6 |
| | (3) necrobiotic regions in the wall | +/4    ++/2 | 0/6 | 0/6 |
| | (4) infiltration of adventitia with lymphoid cells | 0/2    +/4 | 0/4 +/2 | 0/4    +/2 |
| | (5) changes in the endothelium | 0/2 +/2 ++/2 | 0/4 +/2 | 0/4    +/2 |
| | Changes in the cardyomyocytes | | | |
| 5 | (1) granular-lumpy decomposition | +/4    +/2 | 0/2 +/3 ++/1 | 0/3 +/2 +++/1 |
| | (2) nuclei (pyknosis) | 0/3 +/2 +++/1 | 0/3 +/2 ++/1 | 0/3 +/2 ++/1 |
| | (3) necrosis of 3-5 cells | 0/2 ++/2 +++/2 | 0/4 +/2 | 0/3 +/1 ++/2 |
| | (4) necrosis of more than 5 cells | 0/2 +/2 ++/2 | 0/6 | 0/6 |
| | (5) eosinophilia | ++/4    +++/2 | 0/3 +/2 ++/1 | 0/3 +/2 ++/1 |
| | (6) contructure type changes (polarization light) | +/1 ++/2 +++/3 | 0/2 +/3 ++/1 | 0/3 ++/2 +++/1 |
| | Changes in the interstitial tissue | | | |
| 6 | (1) edema | 0/5    +/1 | 0/6 | 0/5    +/1 |
| | (2) diffusive round-cell infiltration | 0/4    +/2 | +/3    ++/3 | 0/3 +/1 ++/2 |
| | (3) large foci of round-cell infiltrates and propagation of the granular tissue | +/1 ++/1 +++/4 | +/2 ++/3 +++/1 | +/2 ++/1 +++/3 |

| Nos | 5 | 6 | 7 | 8 |
|---|---|---|---|---|
| 1 | | 8th day | 8th day | 8th day |
| 2 | Number of animals | 6 | 6 | 6 |
| 3 | Group | adrenaline (control) | Adrenaline + the preparation of this invention | Adrenaline + finoptin |
| | Changes in the myocardial vessels | | | |
| 4 | (1) plethora of the vessels | 0/6 | +/1    0/5 | 0/6 |
| | (2) wall necrosis | 0/6 | 0/6 | 0/6 |
| | (3) necrobiotic regions in the wall | +/1    0/5 | 0/6 | 0/6 |

TABLE 5-continued

| | | | | | | | | | |
|---|---|---|---|---|---|---|---|---|---|
| | (4) infiltration of the adventitia with lymphoid cells | ++/1 | +/1 | 0/4 | | 0/6 | | +/3 | 0/3 |
| | (5) changes in the endothelium | ++/2 | | 0/4 | 0/4 | | +/2 | ++/2 +/1 | 0/2 |
| | Changes in cardiomyocytes | | | | | | | | |
| 5 | (1) nuclei (pyknosis) | | 0/6 | | | 0/6 | | 0/6 | |
| | (2) granular-lumpy decomposition | +++/3 | | ++/3 | ++/2 | | 0/4 | ++/3 +/2 | 0/1 |
| | (3) necrosis of 3-5 cells coagulation type) | ++/2 | +/2 | 0/2 | ++/1 | +/1 | 0/4 | ++/4 | 0/2 |
| | (4) necrosis of more than 5 cells | 0/4 | | +/2 | | 0/6 | | 0/6 | |
| | (5) eosinophilia | +++/3 | | ++/3 | ++/1 | +/2 | 0/3 | +++/1 ++/2 | 0/3 |
| | (6) contracture type changes (polarization light) | +++/3 | | ++/3 | ++/2 | +/1 | 0/3 | ++/3 | 0/3 |
| | Changes in the interstitial tissue | | | | | | | | |
| | (1) edema | | 0/6 | | | 0/6 | | 0/6 | |
| | (2) diffusive round-cell infiltration | +/2 | +/1 | 0/4 | | 0/6 | | 0/6 | |
| | (3) scarring granuloma | ++/4 | | +++/2 | +++/1 | ++/2 | 0/3 | +++/3 ++/1 | 0/2 |

| Nos | | 9 | 10 | 11 | 12 |
|---|---|---|---|---|---|
| 1 | | 12th day | 12th day | 12th day | 12th day |
| 2 | Number of animals | 6 | 6 | 6 | 6 |
| 3 | Group | adrenaline (control) | | Adrenaline + preparation of this invention | Adrenaline + finoptin |
| | Changes in the myocardial vessels | | | | |
| 4 | (1) plethora of the vessels | 0/6 | 0/5 | +/1 | 0/6 |
| | (2) wall necrosis | 0/6 | | 0/6 | 0/6 |
| | (3) necrobiotic regions with changes in the vessel wall | 0/6 | | 0/6 | 0/6 |
| | (4) infiltration of the adventitia with lymphoid cells | +/5 | 0/1 | 0/5 | 0/5 |
| | (5) changes in the endothelium | ++/2 | 0/4 +/1 | 0/5 | ++/1 0/5 |
| | Changes in cardiomyocytes | | | | |
| 5 | (1) Nuclei (pykhnosis) | 0/6 | | 0/6 | 0/6 |
| | (2) granular-lumpy decomposition | ++/1 | +/5 ++/3 | 0/3 | ++/3 +/1 0/2 |
| | (3) necrosis of 3-5 cells | ++/4 | +/2 +/1 | 0/5 | ++/1 +/2 0/3 |
| | (4) necrosis of more than 5 cells | 0/6 | | 0/6 | 0/6 |
| | (5) eosinophilia | ++/5 | 0/1 ++/3 | 0/3 | ++/3 0/3 |
| | (6) contracture type changes (polarization light) | +++/2 | ++/3 0/1 ++/2 | 0/4 | +++/1 +/3 0/2 |
| | Changes in the interstitial tissue | | | | |
| 6 | (1) edema | 0/6 | | 0/6 | 0/6 |
| | (2) diffusive round-cell infiltration | 0/6 | | 0/6 | 0/6 |
| | (3) scarring granuloma | ++/3 | +/3 ++/2 +/1 | 0/3 | ++/2 +/3 0/1 |

| Nos | | 13 | 14 | 15 | 16 |
|---|---|---|---|---|---|
| 1 | | 19th day | 19th day | 19th day | 19th day |
| 2 | Number of animals | 5 | 5 | 5 | 5 |
| 3 | Group | adrenaline (control) | | Adrenaline + the preparation of this invention | Adrenaline + finoptin |
| | Changes in the myocardial vessels | | | | |
| 4 | (1) plethora of the vessels | 0/5 | | +/4 | 0/5 |
| | (2) wall necrosis | 0/5 | | 0/5 | 0/5 |
| | (3) necrobiotic regions with changes in the vessel wall | 0/5 | | 0/5 | 0/5 |
| | (4) infiltration of the adventitia with lymphoid cells | +/5 | | 0/5 | 0/5 |
| | (5) changes in the endothelium | 0/3 | ++/2 | 0/5 | +/1 0/4 |
| | Changes in cardiomyocytes | | | | |
| 5 | (1) nuclei (pyknosis) | | 0/5 | 0/5 | 0/5 |
| | (2) granular-lumpy decomposition | ++/3 | +++/2 0/2 | +/2 ++/1 | 0/1 +/3 ++/1 |
| | (3) necrosis of 3-5 cells | +/1 | ++/4 0/3 | +/2 | 0/2 ++/2 |
| | (4) necrosis of more than 5 cells | | 0/5 | 0/5 | 0/5 |
| | (5) eosinophilia | +/1 | ++/4 0/2 | +/3 | 0/3 +/1 ++/1 |
| | (6) contracture type changes (polarization light) | ++/1 | +++/4 0/2 | +/3 | 0/2 +/2 ++/1 |
| | Changes in the interstitial tissue | | | | |
| 6 | (1) growth of the connective tissue (young) | +/4 | ++/1 0/3 | +/2 | 0/1 +/3 ++/1 |
| | (2) coarse connective tissue | ++/5 | 0/2 | +/1 ++/2 | 0/1 +/2 ++/2 |

TABLE 5-continued (granulation type scarring)

Note:
Absence of the feature - 0
The feature is less pronounced - +
The feature is moderately pronounced - ++
The feature is strongly pronounced - +++
Figures stand for the number of animals with the given feature.

What is claimed is:

1. A pharmaceutical preparation for the treatment of hypertensive disease and myocardial infarction comprising as an active ingredient, a therapeutically effective amount of (1,1-dimethyl-3-oxopyrazolidin-1-io-4-yl) acetate of the following formula:

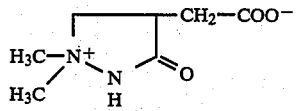

and a pharmaceutically acceptable vehicle.

2. A pharmaceutical preparation as claimed in claim 1 for the administration by injection which comprises the active ingredient in an amount of from 1 to 2.5% by weight.

3. A pharmaceutical preparation as claimed in claim 2 which comprises as the pharmaceutically acceptable vehicle a solvent selected from the group consisting of distilled water and an isotonic solution.

4. A pharmaceutical preparation as claimed in claim 1 for administration perorally which comprises the active ingredient in an amount of 0.4 to 0.45 g per dose.

5. A pharmaceutical preparation as claimed in claim 1, wherein the pharmaceutically acceptable vehicle is a filler selected from the group consisting of starch, silica and magnesium stearate.

6. A pharmaceutical preparation as claimed in claim 1 for administration sublingually which comprises the active ingredient in an amount of 0.4 to 0.45 g per dose.

7. A pharmaceutical preparation as claimed in claim 1 which is in the form of a tablet.

8. A pharmaceutical preparation as claimed in claim 1 which is in the form of a capsule.

* * * * *